(12) United States Patent
Takahashi et al.

(10) Patent No.: US 8,531,672 B2
(45) Date of Patent: Sep. 10, 2013

(54) LUBRICANT DETERIORATION DETECTOR AND BEARING ASSEMBLY EQUIPPED WITH SUCH DETECTOR

(75) Inventors: Toru Takahashi, Iwata (JP); Kentarou Nishikawa, Iwata (JP)

(73) Assignee: NTN Corporation, Osaka (JP)

( * ) Notice: Subject to any disclaimer, the term of this patent is extended or adjusted under 35 U.S.C. 154(b) by 380 days.

(21) Appl. No.: 12/585,794

(22) Filed: Sep. 24, 2009

(65) Prior Publication Data

US 2010/0014087 A1    Jan. 21, 2010

Related U.S. Application Data

(63) Continuation of application No. PCT/JP2008/000523, filed on Mar. 11, 2008.

(30) Foreign Application Priority Data

Mar. 26, 2007    (JP) .................................. 2007-078410

(51) Int. Cl.
*F16C 41/00*    (2006.01)
*G01N 33/26*    (2006.01)

(52) U.S. Cl.
USPC ............... 356/442; 73/10; 73/53.05; 384/448

(58) Field of Classification Search
USPC ............ 356/442; 73/10, 61.69, 61.48, 61.59, 73/61.68, 61.56
See application file for complete search history.

(56) References Cited

U.S. PATENT DOCUMENTS

| 5,245,200 | A | 9/1993 | Fladda |
| 6,324,899 | B1 * | 12/2001 | Discenzo ..................... 73/53.05 |
| 2001/0054304 | A1 * | 12/2001 | Heilenkotter ..................... 73/10 |
| 2003/0160973 | A1 | 8/2003 | Nakayama et al. |

FOREIGN PATENT DOCUMENTS

| DE | 10 2005 001 850 A1 | 7/2006 |
| EP | 0 423 367 A1 | 4/1991 |
| JP | 03-197848 | 8/1991 |
| JP | 09-068496 | 3/1997 |
| JP | 09-154797 | 6/1997 |
| JP | 11-337487 | 12/1999 |
| JP | 2000-130240 | 5/2000 |
| JP | 2004-293776 | 10/2004 |
| JP | 2004-340806 | 12/2004 |
| JP | 2005-345132 | 12/2005 |
| WO | 90/13018 | 11/1990 |

OTHER PUBLICATIONS

International Search Report for PCT/JP2008/000523, mailed Jun. 17, 2008.

(Continued)

*Primary Examiner* — Gregory J Toatley
*Assistant Examiner* — Rebecca C Bryant (57) ABSTRACT

A lubricant deterioration detecting device includes an arcuate optical fiber having one end positioned in face-to-face relation with a light emitting element and also having the opposite end positioned in face-to-face relation with a light receiving element, and a measuring gap for intervening a lubricating agent is provided in a portion of the arcuate optical fiber. In the vicinity of the measuring gap, a resistance element, the amount of deformation of which varies with change in state of lubrication performed with the lubricating agent, is provided for flowing of the lubricating agent within the measuring gap.

4 Claims, 6 Drawing Sheets

(56) References Cited

OTHER PUBLICATIONS

English Translation of the International Preliminary Report on Patentability mailed Oct. 8, 2009 and issued in corresponding International Patent Application PCT/JP2008/000523.
Japanese Decision of Grant issued Sep. 20, 2011 in corresponding Japanese Patent Application 2007-078410.
Chinese Office Action issued Jul. 20, 2011 in corresponding Chinese Patent Application 200880009813.X.
Chinese Office Action mailed Mar. 19, 2012 issued in corresponding Chinese Patent Application No. 200880009813.X.
Partial English Translation of Chinese Office Action mailed Jun. 10, 2010 issued in corresponding Chinese Patent Application No. 200880009813.X.
Partial English Translation of Chinese Office Action mailed Sep. 20, 2011 issued in corresponding Chinese Patent Application No. 200880009813.X.
Chinese Office Action issued Aug. 24, 2012 in corresponding Chinese Patent Application No. 200880009813.X.
European Search Report dated Mar. 15, 2010 issued in corresponding European Patent Application 08720409.5.
Partial English Translation of Chinese Office Action mailed Apr. 6, 2011 issued in corresponding Chinese Patent Application No. 200880009813.X.

\* cited by examiner

DIRECTION OF FLOW OF LUBRICANT ←

Fig. 5B

DIRECTION OF FLOW OF LUBRICANT →

Prior Art

LUBRICANT DETERIORATION DETECTOR AND BEARING ASSEMBLY EQUIPPED WITH SUCH DETECTOR

CROSS-REFERENCE TO RELATED APPLICATIONS

This application is a U.S. continuation application filed under 35 U.S.C. §111(a) claiming priority benefit of International Application PCT/JP2008/000523, filed on Mar. 11, 2008, which claims earlier priority benefit to Japanese Patent Application No. 2007-078410 filed in Japan on Mar. 26, 2007, the disclosures of which are incorporated herein by reference.

BACKGROUND OF THE INVENTION

The present invention relates to a lubricant deterioration detecting device for detecting the status of deterioration a lubricant resulting from admixture of an alien substance and also to a detector equipped bearing assembly equipped with such lubricant detection detecting device such as, for example, a lubricant deterioration detector incorporated bearing assembly for use in railway vehicles, automotive vehicles, wind mill facilities and industrial plant facilities or the like.

BACKGROUND ART

In the bearing assembly filled with a lubricant, an insufficient lubrication occurs once the lubricant (such as, for example, a grease or oil) within the bearing assembly is deteriorated, resulting in a reduction in lifetime of the bearing assembly. Determination of the occurrence of the insufficient lubrication in reference to the status of vibration occurring in the bearing assembly is carried out when and after an operating abnormality has occurred as a result of expiration of the lifetime of the bearing assembly and is, accordingly, incapable of detecting the presence or absence of an abnormality in lubrication at an early time. In view of this, it has been desired to monitor the status of the lubricant within the bearing assembly regularly or in real time so that the occurrence of the abnormality and/or the time of maintenance can be predicated.

A major cause of deterioration of the lubricant may be enumerated an admixture of a powdery wear debris, which is produced as the bearing assembly is used, with the lubricant.

For detecting the status of wear of the bearing assembly, a sensor incorporated bearing assembly has been suggested, in which an electrode is arranged inside a sealing member of the bearing assembly so that the electrical characteristic of the lubricant resulting from the admixture of the wear debris can be detected in terms of a change in resistance, electrostatic capacitance, magnetic resistance or impedance. (See, for example, the Patent Document 1 listed below.)
[Patent Document 1] Japanese Laid-open Patent Publication No. 2004-293776

However, since the sensor incorporated bearing assembly disclosed in the above mentioned Patent Document 1 is so designed that the electrical characteristic of the lubricant can be detected, no change in characteristic can be detected and, thus, difficulty often occurs in detecting the inclusion of the alien substance unless a condition is established in which conduction occurs as a result of inclusion of a substantial amount of wear debris.

Figure 10:
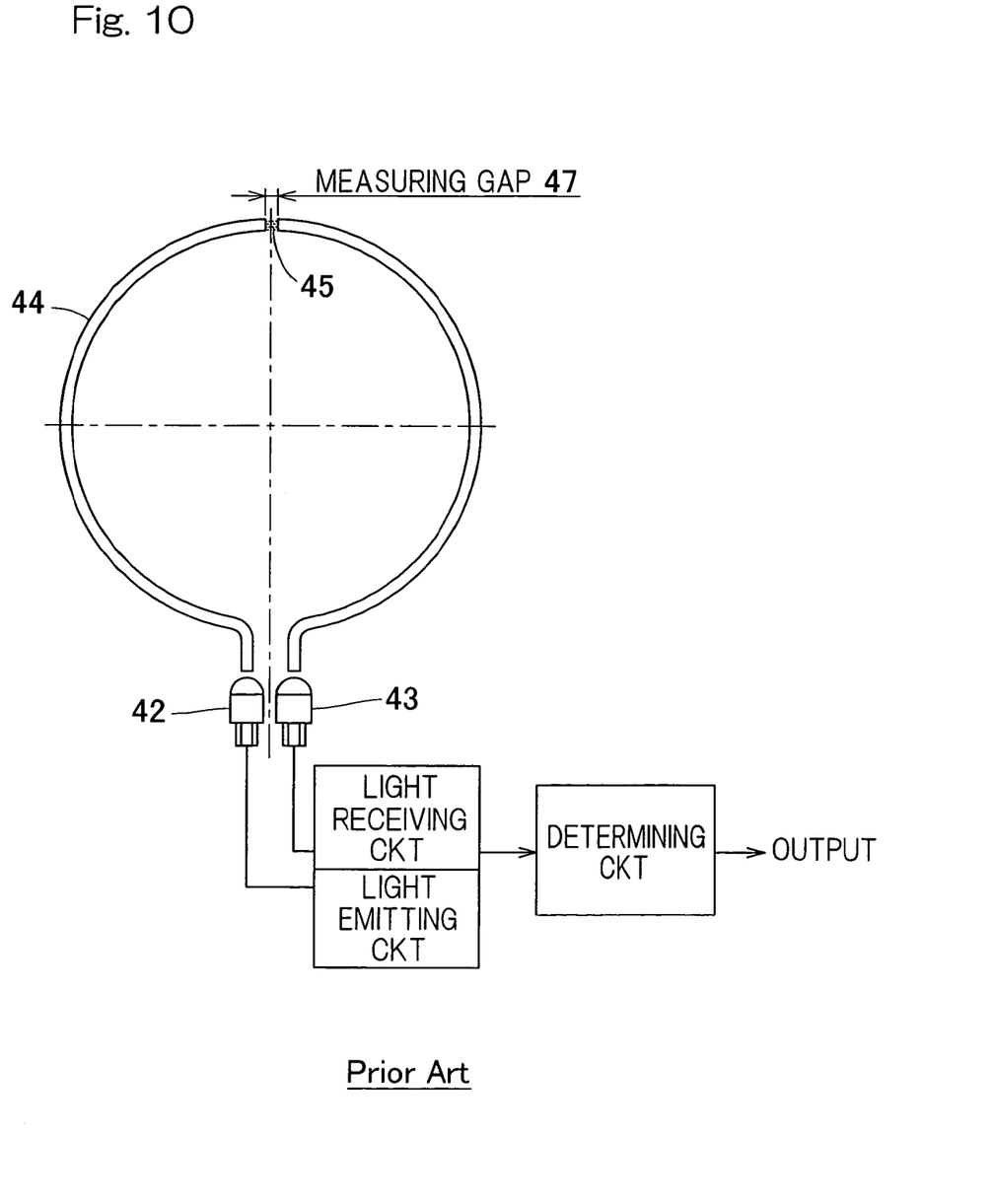
FIG. 10 is a schematic structural diagram showing the conventional example of the lubricant deterioration detecting device.

In an attempt to resolve the foregoing problem, the optical system, for example, has been conceived, in which as shown in FIG. 10, the use is made of an optical fiber 44 representing a split ring shape and having one end positioned in face-to-face relation with a light emitting element 42 and also having the opposite end positioned in face-to-face relation with a light receiving element 43, and a measuring gap 47 defined in a portion of the circumference of the ring shaped optical fiber 44 for receiving a lubricating agent 45 inserted therein.

According to the optical system of the structure shown in FIG. 10, rays of light emitted from the light emitting element 42 travel through the lubricating agent 45, then intervening within the measuring gap 47, by way of the optical fiber 44 and are subsequently detected by the light receiving element 43 so that the amount of foreign matter such as, for example, powdery iron admixed in the lubricating agent 45 can be estimated from the amount of light passed across the lubricating agent 45 and detected by the light receiving element 43.

It has, however, been found that where the optical sensor system of the type discussed above is incorporated in a bearing assembly for the purpose of detecting the status of deterioration of the lubricating agent filled inside the bearing assembly, the optical fiber 44 tends to be loaded as a result of a flow of the lubricating agent since no protection is made to the optical fiber 44. For this reason, it is highly possible that the output will fluctuate in correspondence with movement of the optical fiber 44, with the consequence that no detection can be accomplished with a stabilized precision. Also, fixing of the optical fiber 44 requires a hard work.

One approach to avoid the movement of the optical fiber 44 resulting from a flow of the lubricating agent may be contemplated, in which the use is made of a covering for covering a portion of the optical fiber 44 excluding a portion thereof in the vicinity of the measuring gap 47.

In this case, however, the covering used tends to limit the movement of the lubricating agent within the bearing assembly, which takes place accompanied by the rotation of rolling elements and a retainer, and, therefore, the lubricating agent will find difficulty in entering the measuring gap 47, failing to achieve the stabilized detection with a high precision.

SUMMARY OF THE INVENTION

An object of the present invention is to provide a lubricant deterioration detecting device capable of being simply and compactly mounted on a bearing assembly and, also, capable of achieving a stabilized detection of the status of deterioration of the lubricating agent within the bearing assembly with a high precision, and also to provide a detector equipped bearing assembly equipped with the lubricant deterioration detecting device.

The lubricant deterioration detecting device of the present invention is a lubricant deterioration detecting device of a type including an optical fiber of an arcuate shape having one end positioned in face-to-face relation with a light emitting element and also having the opposite end positioned in face-to-face relation with a light receiving element, a measuring gap defined in a portion of the arcuate optical fiber for receiving a lubricating agent inserted therein, and a deformable resistance element provided in proximity to the measuring gap, of which amount of deformation changes with change of the state of lubrication with the lubricating agent.

According to this construction, when the state of lubrication changes, the amount of deformation of the resistance element provided in proximity to the measuring gap changes. As a result of this deformation of the resistance element, the lubricating agent present in the vicinity of the resistance element also moves accompanied by the deformation of the resistance element. The lubricating agent then ingresses newly into a space left as a result of this movement. For this reason, the lubricating agent having been present in the measuring gap is superseded and the lubricating agent working to lubricate at all times will become an object to be detected, making it possible to achieve a stabilized detection of the status of deterioration of the lubricating agent with a high precision. Also, since it is basically made up of the optical fiber and the light emitting and receiving elements, it can be installed easily and compactly inside the bearing assembly.

In the practice of the present invention, the resistance element referred to above may be a leaf spring-like member or a hinge structure having its angle variable at a hinge portion thereof. If the resistance element is employed in the form of the leaf spring-like member or the hinge structure having its angle variable at the hinge portion thereof, the resistance element can change easily in response to a change in state of lubrication and/or a flow of the lubricating agent.

In the present invention, the resistance element has a planimetric shape (a shape in a plan view), which may be effective to move the lubricating agent in at least two of a direction along an arc center axis relative to the arcuate shape of the optical fiber, a radial direction thereof and a circumferential direction thereof.

Where within an annular bearing space present inside the rolling bearing assembly, the optical fiber referred to above is disposed with its arc following the annular bearing space, and if the resistance element is of a shape capable of moving the lubricating agent in at least two of the direction along an arc center axis relative to the arcuate shape of the optical fiber, the radial direction thereof and the circumferential direction thereof, movement of the lubricating agent into and out of the measuring gap can be facilitated.

The detector equipped bearing assembly of the present invention is of a type, in which the lubricant deterioration detecting device of any one of the foregoing constructions according to the present invention is fitted to a rolling bearing assembly with the resistance element positioned within the bearing space delimited between inner and outer rings of the rolling bearing assembly.

According to this construction, movement of the lubricating agent into the measuring gap of the optical fiber can be facilitated and the detection of the status of deterioration of the lubricating agent inside the bearing assembly can be accomplished stably and precisely with the lubricant deterioration detecting device.

As a result thereof, the status of deterioration of the lubricating agent filled inside the bearing assembly can be accurately detected on a real time basis. Therefore, the necessity of replacement of the lubricating agent can be determined prior to the occurrence of an abnormality in operation of the bearing assembly and any possible damage to the bearing assembly, which would result from failure to lubricate the bearing assembly, can be avoided. Also, since the necessity of replacement of the lubricating agent can be determined in reference to an output from the lubricant deterioration detecting device, the amount of the lubricating agent to be disposed of prior to the expiration date for use of such lubricating agent can be reduced.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DESCRIPTION OF THE PREFERRED EMBODIMENTS

Figure 1:
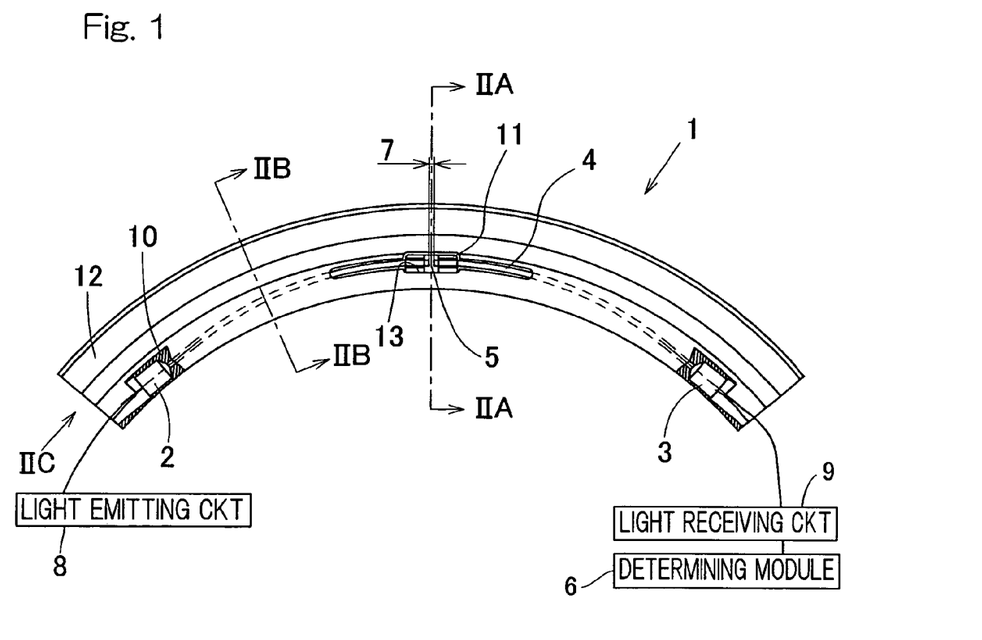
FIG. 1 is a schematic structural diagram of a lubricant deterioration detecting device according to a preferred embodiment of the present invention.

One preferred embodiment of the present invention will be described in detail with particular reference to FIGS. 1 to 5A and 5B. FIG. 1 illustrates a schematic structural diagram of a lubricant deterioration detecting device according to this embodiment. This lubricant deterioration detecting device 1 is of a type adapted to be mounted on a bearing assembly for detecting the status of deterioration of a lubricating agent filled inside the baring assembly and includes a light emitting element 2, a light receiving element 3, an arcuate shaped optical fiber 4 and a determining module 6 for determining the status of deterioration in reference to an output from the light receiving element 3. The optical fiber 4 has one end positioned in face-to-face relation with a light emitting face of the light emitting element 2 and also has the opposite end positioned in face-to-face relation with a light receiving face of the light receiving element 3. Also, a measuring gap 7 for receiving a lubricating agent 5 therein is defined in a portion of the circumference of the optical fiber 4.

In view of the fact that the measuring gap 7 for receiving the lubricating agent 5 forming an object to be detected, which agent 5 is intervened therein, is provided in that circumferential portion of the optical fiber 4, rays of light emitted from the light emitting element 2 are transmitted through the optical fiber 4 so as to pass across the lubricating agent 5 and are subsequently received by the light receiving element 3 further through the optical fiber 4.

For the light emitting element 2 referred to above, any of LED, EL and organic EL elements can be employed and is driven by a light emitting circuit 8. For the light receiving element 3, any of a photodiode and a phototransistor can be employed and the amount of light received by this light receiving element 3 is detected by a light receiving circuit 9 then receiving an output from the light emitting element 3.

Figure 2A:
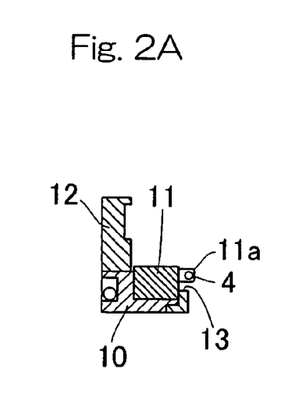
FIG. 2A is a cross sectional view taken along the line IIA-IIA in FIG. 1.
Figure 2B:
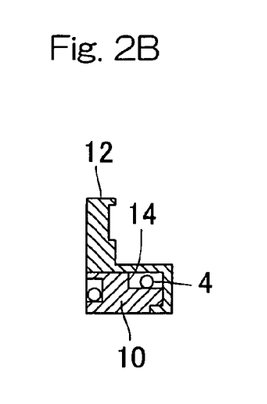
FIG. 2B is a cross sectional view taken along the line IIB-IIB in FIG. 1.
Figure 2C:
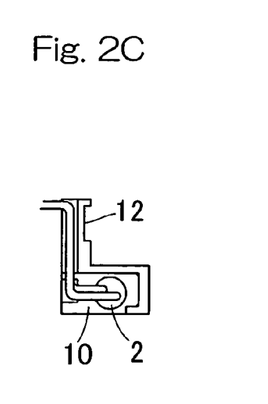
FIG. 2C is a side view as viewed in a direction IIC conforming to the arrow headed line in FIG. 1.

The optical fiber 4 is fitted to an arcuate covering 12 of a diameter substantially equal to that of the optical fiber 4 through two, fixtures 10 and 11. The arcuate covering 12 is a member for covering a portion of the optical fiber 4, excluding the measuring gap 7 and its vicinity to thereby protect the optical fiber 4 from a load brought about by a flow of the lubricating agent 5 forming an object to be detected and is, as best shown in FIG. 2B in the cross sectional view taken along the line IIB-IIB in FIG. 1, made of a rigid material, for example, a plastic or metallic material, having a sectional shape generally similar to the shape of a figure "S". More specifically, the covering 12 is so designed as to cover at least one side (a right side in the example shown in FIG. 2B) in a direction of the center axis of the arcuate shape relative to the arcuate optical fiber 4. In the case the lubricant deterioration detecting device 1 to be incorporated in the bearing assembly, the arcuate covering 12 is so arranged as to permit a front surface side (a right side surface in the example shown in FIG. 2B) thereof to be exposed to the lubricating agent filled in the bearing assembly.

One of the fixtures 10 for fixing the optical fiber 4 is an arcuate member adapted to be joined to a lower half of a rear surface (a left side surface in the example shown in FIG. 2B) of the covering 12 and the optical fiber 4 has its opposite ends each fixed to the fixture 10 and the light emitting and receiving elements 2 and 3 are also fixed to the fixture 10. The other of the fixtures 11 for fixing the optical fiber 4 is, as shown in FIG. 2A showing the cross sectional view taken along the line IIA-IIA in FIG. 1, fixed to the front surface side of the fixture 10 and a portion of the optical fiber 4 in the vicinity of the measuring gap 7 is fixed to and, hence, positioned by this second fixture 11. Thus, since that portion in the vicinity of the measuring gap 7 is fixed by the fixture 11 separate from the fixture 10 for fixing respectively the opposite ends of the optical fiber 4, positioning of the measuring gap 7 can be facilitated, allowing the lubricant deterioration detecting device 1 to be assembled easily. It is to be noted that the fixture 11 may be fixed directly to the arcuate covering 12, not to the fixture 10. Also, instead of the use of those separate fixtures 10 and 11, a single fixture may be employed.

Figure 3:
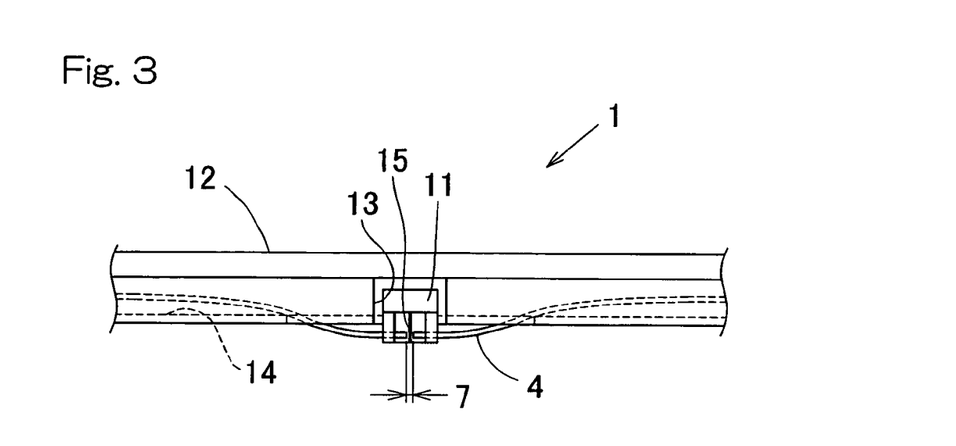
FIG. 3 is a fragmentary top plan view of the lubricant deterioration detecting device.

A portion of the arcuate covering 12 intermediate of the circumference thereof, which corresponds in position to the measuring gap 7 in the optical fiber 4, is provided with a slit shaped opening 13 extending in a direction circumferentially thereof as shown in FIG. 1 in a front elevational representation, wherefore the measuring gap 7 is exposed to the lubricating agent within the bearing assembly. As shown in FIG. 3 in a top plan view, the fixture 11 is of a structure, in which a portion supporting a proximate area of the measuring gap 7 in the optical fiber 4 is rendered to be forked legs 11a protruding from the opening 13 of the arcuate covering 12 towards a front surface side of the arcuate covering 12. Accordingly, that portion proximate to the measuring gap 7 in the optical fiber 4 is caused to protrude outwardly from the arcuate covering 12.

Because of the above described construction, the front surface side of the fixture 10 for fixing the opposite ends of the optical fiber 4, the light emitting element 2 and the light receiving element 3 is covered by the covering 12. Also as shown in FIG. 2B, a portion other than the measuring gap 7 in the optical fiber 4 is arranged within an arcuate space 14 defined between the covering 12 on the front surface side and the fixture 10 on the rear surface side. Accordingly, the optical fiber 4, the light emitting element 2 and the light receiving element 3 are protected from a load imposed as a result of a flow of the lubricating agent 5.

Fixing of the fixtures 10 and 11 to the arcuate covering 12, or fixing of the fixture 11 to the other fixture 10, is carried out by means of a coupling process, which is one or more of press-fitting, bonding and welding. Accordingly, incorporation of the lubricant deterioration detecting device 1 into the bearing assembly can be accomplished easily.

Figure 4A:
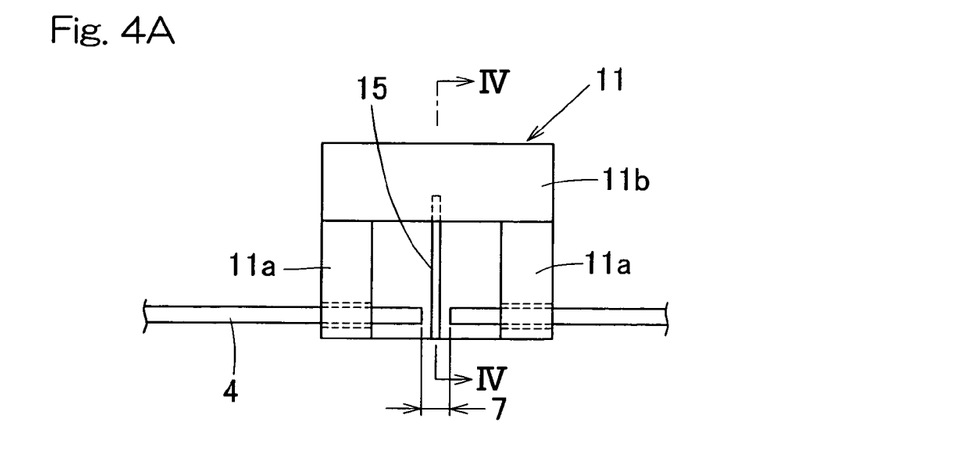
FIG. 4A is a top plan view, on an enlarged scale, showing a measuring gap in an optical fiber.
Figure 4B:
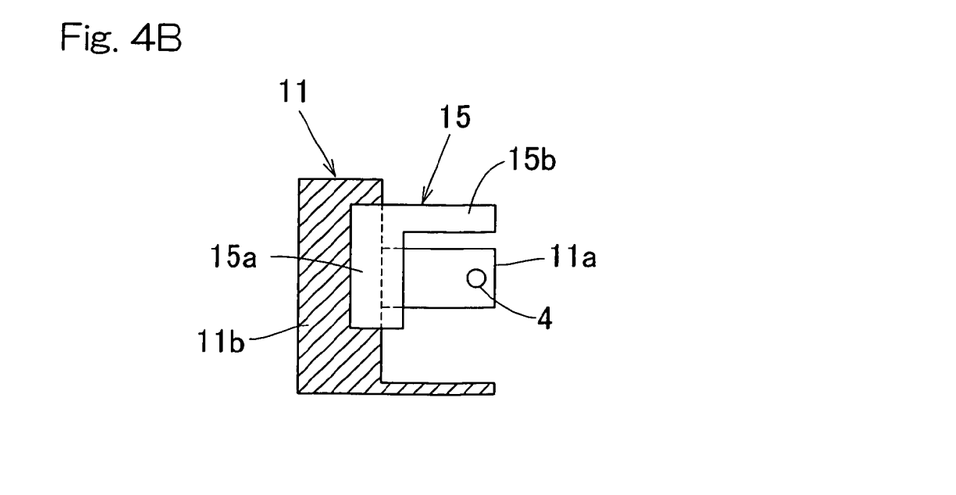
FIG. 4B is a cross sectional view taken along the line IV-IV in FIG. 4A.

That portion proximate to the measuring gap 7 in the optical fiber 4 is provided with a resistance element 15 for flow of the lubricating agent 5 within the measuring gap 7. This resistance element 15 is rendered to be a deformable member, the amount of deformation of which varies with changing of the state of lubrication performed by the lubricating agent 5, forming an object to be detected, within the bearing assembly and is, in the illustrated embodiment, rendered to be a leaf spring-like member. More specifically, the resistance element 15, which is the leaf spring-like member, is of a generally L-shaped configuration having a deformable piece 15a protruding at right angles to a base end 15a thereof, as best shown in an enlarged top plan view in FIG. 4A and an enlarged sectional view in FIG. 4B, in which the base end 15a is supported by a front surface of a body 11b of the fixture 11 with its plate face lying perpendicular to the circumferential direction of the arcuate optical fiber 4 whereas the deformable piece 15b extends to a position proximate to an upper portion of the measuring gap 7 in the optical fiber 4. It is to be noted that FIG. 4B represents a cross sectional view taken along the line IV-IV in FIG. 4A.

The operation of the above described construction will now be described. When the lubricating agent is new and fresh, the lubricating agent is in a condition nearly transparent and the intensity of rays of light projected from the light emitting element 2 and then passed across the lubricating agent 5 through the optical fiber 4 is therefore high. However, as the amount of foreign matter such as, for example, iron powder (wear debris) admixed in the lubricating agent 5 increases, the intensity of the transmitted rays of light decreases gradually. In view of this, the determining module 6 refers to an output from the light receiving element 3, which is proportional to the intensity of the transmitted rays of light, to detect the amount of the foreign matter admixed in the lubricating agent 5. Since increase of the amount of the foreign matter admixed in the lubricating agent 5 means a progress in deterioration of the lubricating agent 5, it is possible to estimate the status of deterioration of the lubricating agent 5 from the amount of the foreign matter detected. The determining module 6 includes, for example, a relation setting module (not shown), in which the relation between the output of the light receiving element 3 and the status of deterioration of the lubricating agent is preset in the form of a computing equation, table and threshold value, and outputs a quantitative or step by step result of estimation of the status of deterioration by comparing the output of the light receiving element 3 with the preset contents of the relation setting module.

Where the lubricant deterioration detecting device 1 of the structure described hereinbefore is disposed inside, for example, a rolling bearing assembly, between a rolling surface for rolling elements (for example, rollers) and a sealing element at a bearing end portion with the arcuate optical fiber 4 held in coaxial relation with the bearing assembly, the lubricating agent (for example, a grease) present between rolling surfaces is, as an inner ring, the rolling element and a retainer rotate, urged to flow towards the side of the sealing element, that is, the side where the lubricant deterioration detecting device 1 is installed, while moving in a direction conforming to the direction of rotation. The lubricating agent so urged moves towards an inner ring outer peripheral surface, rolling element end faces and outer and inner peripheral surfaces of the retainer in a direction conforming to the direction of rotation and also towards the side of the sealing element. The lubricating agent so moving in the manner described above flows into the measuring gap 7 in the optical fiber 4 of the lubricant deterioration detecting device 1 and, therefore, the state of deterioration of the lubricating agent is estimated by the operation described hereinabove.

Figure 5A:
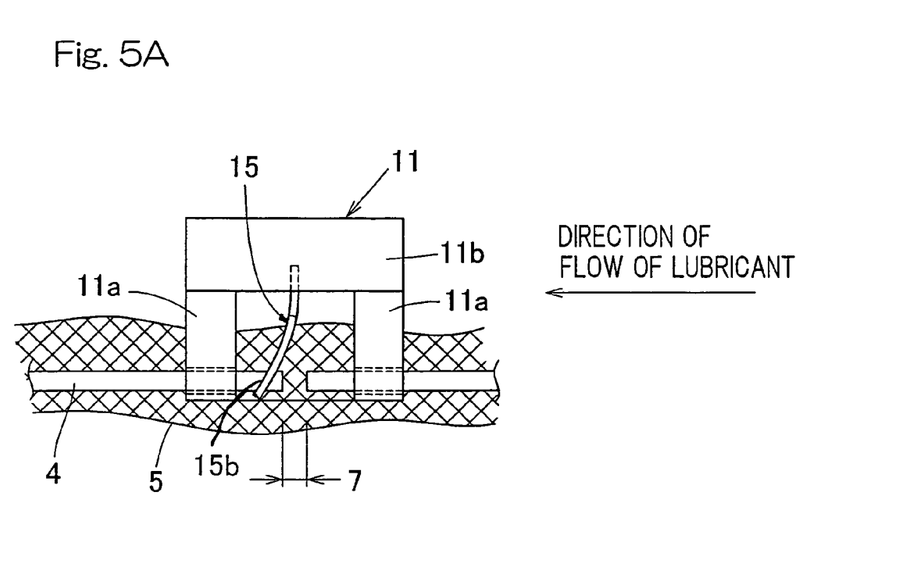
FIGS. 5A and 5B are explanatory diagrams used to explain the operation of the lubricant deterioration detecting device.
Figure 5B:
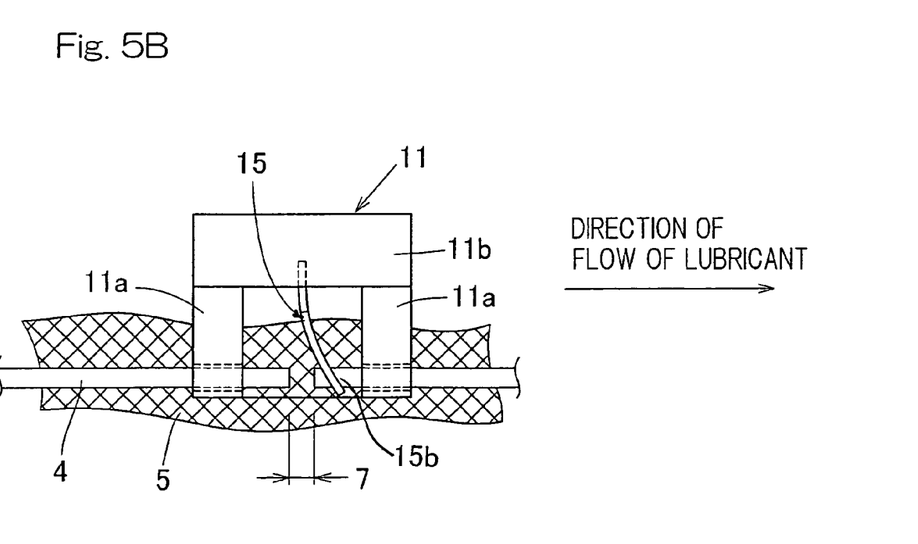

Since, however, the lubricating agent flowing into the measuring gap 7 is hardly discharged from the measuring gap 7 and fills up the measuring gap 7, the lubricating agent newly discharged from the bearing rolling surfaces will hardly flow into the measuring gap 7. However, in the embodiment of the present invention now under discussion, as best shown in FIGS. 5A and 5B, the deformable piece 15b of the resistance element 15 undergoes a bending deformation in the vicinity of the measuring gap 7 (in the vicinity of an upper portion of the measuring gap 7 in the illustrated instance) under the influence of a flow of the lubricating agent 5. In such case, the deformable piece 15b of the resistance element 15 is rendered to have a planimetric shape, which, when deformed, causes the lubricating agent 5 to move in two directions, i.e., in a direction along an arc center axis relative to the arcuate shape of the optical fiber, 5 and a circumferential direction thereof. The direction of deformation of the deformable piece 15b varies depending on the direction in which the lubricating agent 5 flows. In other words, since when the direction of rotation of the bearing assembly is reversed, the direction in which the deformable piece 15b of the resistance element 15 reverses, the lubricating agent 5 present in the vicinity of the measuring gap 7 is removed to allow the space, from which the lubricating agent 5 has been removed, to be supplemented by a new lubricating agent 5. In this way, a flow of the lubricating agent 5 occurs within the measuring gap 7 and, in this measuring gap 7, the lubricating agent is successively supplemented.

As hereinabove described, since in this lubricant deterioration detecting device 1, the arcuate optical fiber has one end positioned in face-to-face relation with the light emitting element 2 and also has the opposite end positioned in face-to-face relation with the light receiving element 3, since the measuring gap 7 is provided in that portion of the optical fiber 4 for interposing the lubricating agent 5, and since the resistance element 15, the amount of deformation of which is variable depending on a change in state of lubrication performed by the lubricating agent, is provided in the vicinity of the measuring gap 7, the lubricating agent 5 which fills up the measuring gap 7 can flow in response to deformation of the resistance element 15 particularly where it is mounted on, for example, the rolling bearing assembly to detect the status of deterioration of the lubricating agent 5 within the bearing assembly. Accordingly, since in this measuring gap 7 the lubricating agent 5 is successively replenished, the lubricating agent 5 actually working to lubricate can be rendered to be an object to be detected at all times and, therefore, it is possible to achieve the detection of deterioration of the lubricating agent stably and with a high precision.

Also, the deformation of the resistance element 15 in this case is not caused by an external manipulation or the like and, therefore, not only is any manipulating mechanism required, but also the lubricant deterioration detecting device 1 can be mounted easily on the bearing assembly or the like with a compact construction and there is no possibility that mounting of the lubricant deterioration detecting device 1 on the bearing assembly will not narrow the space in which the lubricating agent is filled or to be filled.

Figure 6A:
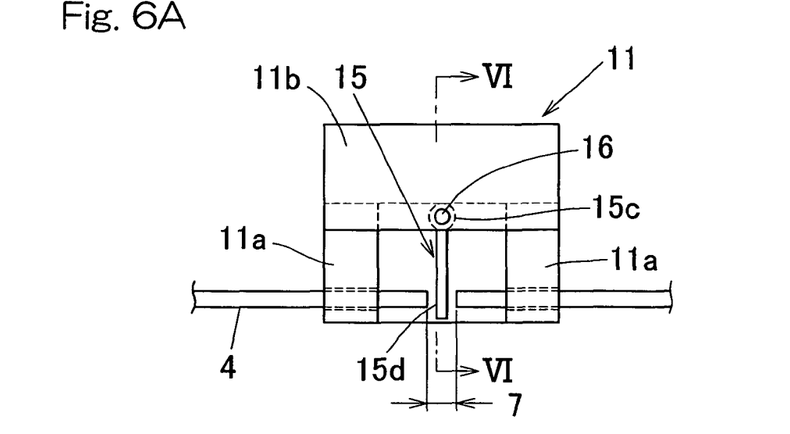
FIG. 6A is a top plan view, on an enlarged scale, showing a portion of the lubricant deterioration detecting device according to another preferred embodiment of the present invention in the vicinity of the measuring gap.
Figure 6B:
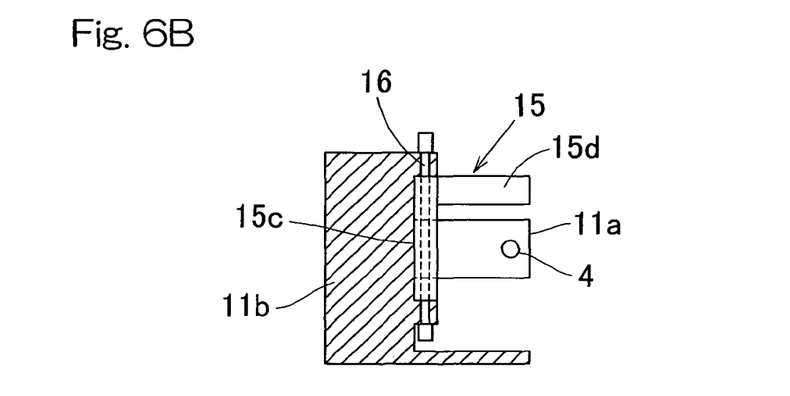
FIG. 6B is a cross sectional view taken along the line VI-VI in FIG. 6A.
Figure 7:
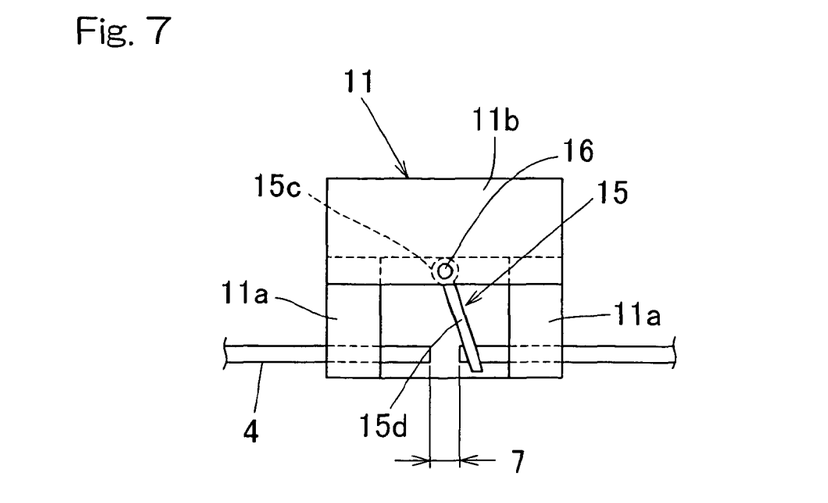
FIG. 7 is an explanatory diagram used to explain the operation of the lubricant deterioration detecting device.

FIGS. 6A and 6B, and FIG. 7 illustrate another preferred embodiment of the present invention. The lubricant deterioration detecting device 1 according to this alternative embodiment is similar to that according to the previously described embodiment, but differs therefrom in that as the resistance element 15 to be employed in the fixture 11 in the embodiment shown in and described with reference to FIG. 1 to FIGS. 5A and 5B, a hinge structure having an angle variable at a hinge portion thereof is employed. More specifically, as shown in an enlarged top plan view and an enlarged sectional view shown in FIGS. 6A and 6B, respectively, the resistance element 15 is rendered to be of a generally L-shaped configuration including a cylindrical hinge portion 15c and a projecting piece 15d protruding outwardly from and lying at right angles to the cylindrical hinge portion 15c; the cylindrical hinge portion 15c is rotatably supported by a pivot pin 16 provided at a front surface of a body 11b of the fixture 11 so as to extend vertically with a plate face of the projecting piece 15d positioned so as to extend perpendicular to the circumferential direction of the arcuate optical fiber 4; and the projecting piece 15d is extended to a position in the vicinity of an upper portion of the measuring gap 7 in the optical fiber 4. Other structural features than those described above are similar to those employed in the previous embodiment shown in and described with reference to FIG. 1 to FIGS. 5A and 5B. It is, however, to be noted that FIG. 6B is a cross sectional view taken along the line VI-VI in FIG. 6A.

In the case of this embodiment, as shown in FIG. 7, the projecting piece 15d of the resistance element 15 displaces angularly about the cylindrical hinge portion 15c in the vicinity of the measuring gap 7 (i.e., in the vicinity of that upper portion of the measuring gap 7 in the illustrated embodiment) in response to a flow of the lubricating agent. Even in this case, the projecting piece 15d of the resistance element 15 is rendered to represent a planimetric shape effective to cause the change in angle thereof to result in movement of the lubricating agent 5 in two directions including a direction parallel to an arc center axis relative to the arcuate shape of the optical fiber 4 and a circumferential direction thereof. The angle of the resistance element projecting piece 15d changes with a direction in which the lubricating agent 5 flows. In other words, if the direction of rotation of the bearing assembly is reversed, the projecting piece 15d of the resistance element 15 pivots and, therefore, the lubricating agent 5 in the vicinity of the measuring gap 7 is removed to allow the lubricating agent 5 to newly fill up the space from which the preceding lubricating agent 5 has been removed. In this way, a flow of the lubricating agent 5 takes place within the measuring gap 7 and, accordingly, the lubricating 5 in the measuring gap 7 is successively replenished.

It is to be noted that in the practice of this embodiment, the hinge portion 15c of the resistance element 15 may be constructed with a coiled spring. In the case of this construction, in a condition in which no load is brought about on the projecting piece 15d by a flow of the lubricating agent, the projecting piece 15d is, by the restoring force of the spring of the hinge portion 15c, restored to the angular position, at which it will not be affected by a flow, and, therefore, change in angle of the projecting piece 15d occurs frequently.

Accordingly, a flow of the lubricating agent 5 within the measuring gap 7 can be promoted further.

Also, in any one of the foregoing embodiments, the deformable piece 15b of the resistance element 15 or the projecting piece 15d of the resistance element 15 has been shown and described as having the planimetric shape effective to move the lubricating agent 5 in the direction conforming to the arc center axis relative to the optical fiber 4 and the circumferential direction thereof, but the planimetric shape may not be limited to such as shown and described. In other words, the planimetric shape of the resistance element may be of any suitable shape, provided that the lubricant agent 5 can be moved in at least two directions selected from the group consisting of the direction conforming to the arc center axis relative to the arc shape of the optical fiber 4, a radial direction thereof and the circumferential direction thereof.

Figure 8:
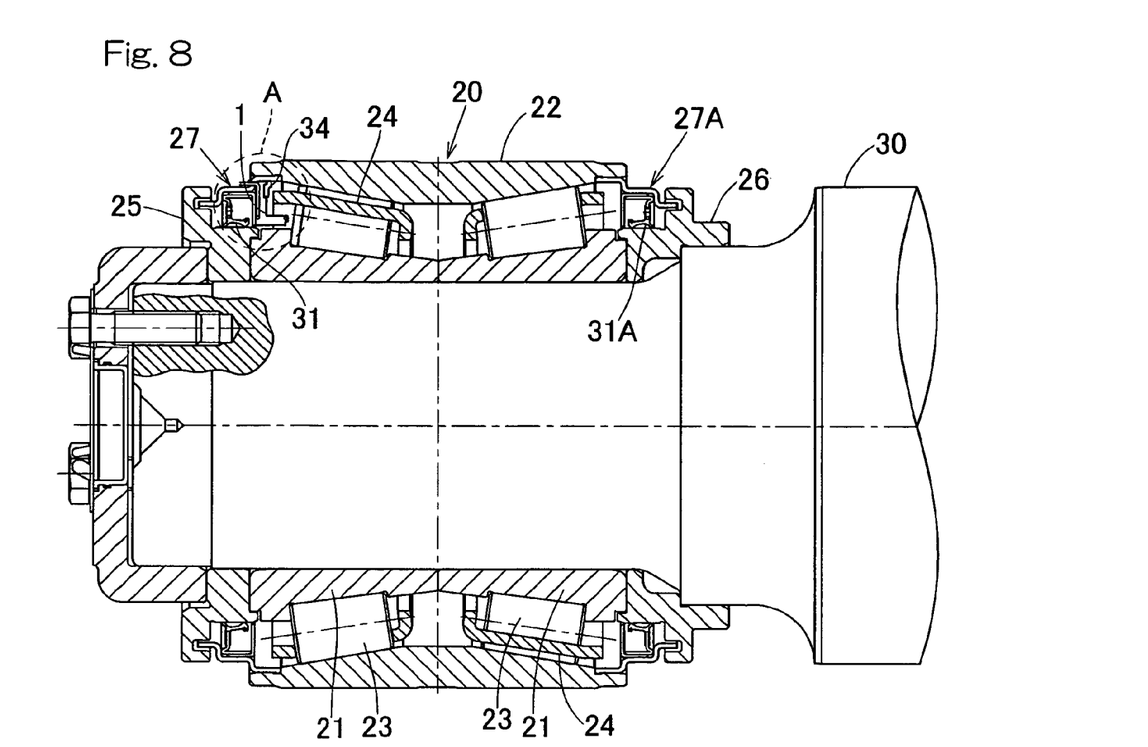
FIG. 8 is a sectional view showing an example of structure of a detector equipped bearing assembly having the lubricant deterioration detecting device of the present invention mounted thereon.
Figure 9:
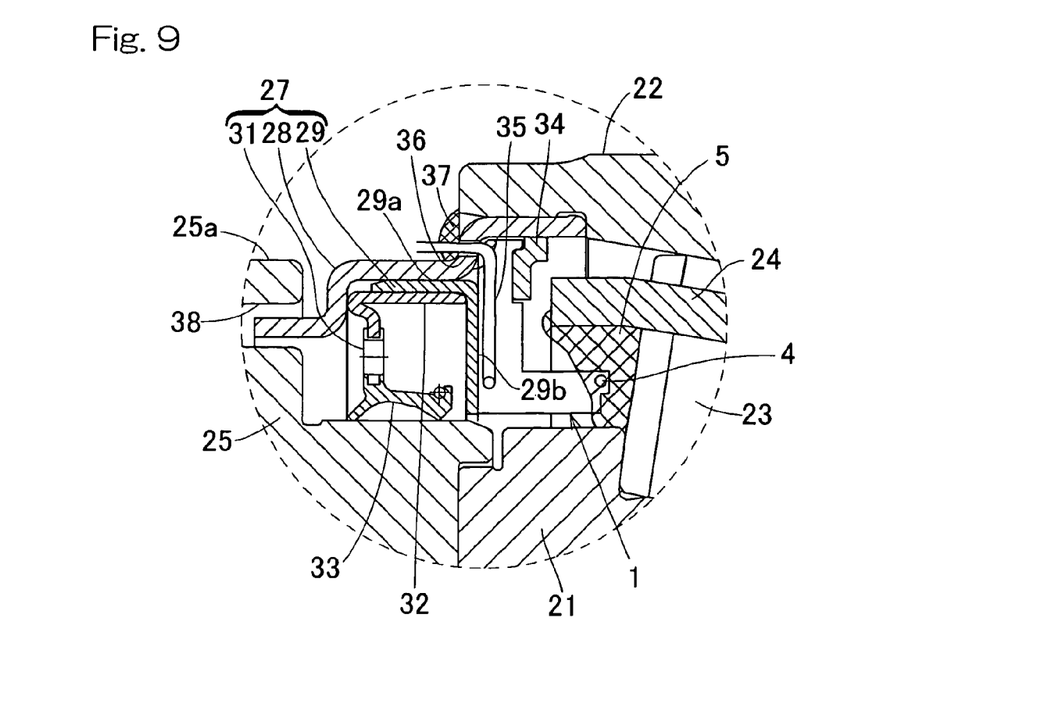
FIG. 9 is a sectional view, on an enlarged scale, showing a sealing unit in the detector equipped bearing assembly.

FIGS. 8 and 9 illustrates an example of a detector equipped bearing assembly, in which the lubricant deterioration detecting device 1 according to the foregoing embodiment of the present invention is in a bearing for use in association with railway vehicles. The detector equipped bearing assembly 20 includes, as best shown in FIG. 8, a slinger 25 and a rear lid 26 that are accessory parts provided in contact with opposite ends of an inner ring 21, respectively, both of the slinger 25 and the rear lid 26 altogether forming a bearing unit for use in association with a railway vehicle. The bearing assembly 20 is in the form of a roller bearing assembly, more specifically in the form of a double row tapered roller bearing assembly and includes split type inner rings 21 and 21 provided for respective rows of rolling elements 23 and 23, an outer ring 22 of one-piece construction, and a retainer 24.

The rear lid 26 is fitted to a wheel axle 30 on a center side rather than the bearing assembly 20 and has its outer periphery held in sliding contact with a bearing sealing element 31A. The slinger 25 is fitted to the wheel axle 30 and has its outer periphery held in sliding contact with a bearing sealing element 31. The lubricating agent is sealed inside the bearing assembly 20 by those bearing sealing elements 31 and 31A arranged on the opposite ends of the bearing assembly 20 and, therefore, a dust control and water resistant properties can be secured.

In this case, a sensor unit (the light emitting element 2, the light receiving element 3, the optical fiber 4, the arcuate covering 12 and others) employed in the lubricant deterioration detecting device 1, excluding a circuit unit (the determining module 6, the light emitting circuit 8 and the light receiving circuit 9), is incorporated into and hence integrated together with a sealing unit 27 including the bearing sealing element 31 referred to previously. FIG. 9 illustrates an enlarged sectional view of an installation portion (A portion) for the sealing unit 27 in FIG. 8.

The sealing unit 27 in this case is made up of an annular seal casing 28 fitted to one end of the bearing outer ring 22, a ring member 29 press fitted into an inner diametric surface of this seal casing 28, and the bearing sealing element 31 press fitted into an inner peripheral surface of the ring member 29. The seal casing 28 is an annular member for covering the bearing sealing element 31 and has a sectional shape having a plurality of steps successively stepped in an axial direction thereof, one end of which is press fined into the inner diametric surface of the bearing outer ring 22, which forms a stationary ring, and is therefore fitted to the bearing outer ring 22. Also, a small diameter step at the opposite end of the seal casing 28 is loosely engaged in a ring shaped groove 38, defined in an inwardly oriented end face of an a flanged portion 25a of the slinger 25, to thereby define a labyrinth between the groove 38 and the small diameter step of the seal casing 28, with which sealing is achieved.

The ring member 29 of a generally L-sectioned configuration having a cylindrical portion 29a is fitted to the seal casing 28 with the cylindrical portion 29a press fitted into an inner diametric surface of an intermediate step in the seal casing 28. A radially inwardly extending upright wall portion 29b of the ring member 29 is so arranged as to form a predetermined labyrinth gap relative to an outer diametric surface of the slinger 25. The bearing sealing element 31 is made up of an annular core metal 32 of an L-sectioned configuration, and an elastic member 33 fixed to an upright wall portion of the annular core metal 32 and is fixed to the seal casing 28 through the ring member 29 with a cylindrical portion of the annular core metal 32 press fitted into an inner peripheral surface of the cylindrical portion 29a of the ring member 29. The elastic member 33 is formed with a radial lip adapted to be slidingly engage an outer diametric surface of the slinger 25.

The lubricant deterioration detecting device 1 is fitted coaxially to the sealing unit 27. More specifically, the arcuate covering 12 of the lubricant deterioration detecting device 1 is engaged in an inner diametric surface of a large diameter step in the seal casing 28 and, by the action of a press fitted ring 34 subsequently press fitted, the lubricant deterioration detecting device 1 is urged over the large diameter step end face of the seal casing 28 and the upright wall portion 29b of the ring member 29 so that the lubricant deterioration detecting device 1 can be axially positioned and fixed in position. When the lubricant deterioration detecting device 1 is positioned and fixed in position in this way, the measuring gap 7 in the optical fiber and the resistance element 15, both shown in FIG. 7, are arranged in the vicinity of large end faces of the rollers 23 on one side radially inwardly of the retainer 24 within a bearing space delimited between the inner and outer rings 21 and 22 shown in FIG. 9.

Since a large amount of the lubricating agent 5 within the bearing assembly are deposited on the inner and outer diametric surfaces of the retainer 24 and the large diameter end faces of the rollers 23 and, accordingly, positioning of the measuring gap 7 in the optical fiber 4 in the manner described hereinabove is effective to facilitate ingress of the lubricating agent 5 into the measuring gap 7 without the fluidity of the lubricating agent 5 being impaired by the arcuate covering 12 of the lubricant deterioration detecting device 1. In addition, since the lubricating agent 5 within the measuring gap 7 flows in response to the resistance element 15 movably provided in the vicinity of the measuring gap 7, the lubricating agent 5 can be successively replenished into and out of the measuring gap 7 and, hence, the lubricating agent 5 actually participating in lubrication can stably enter the measuring gap 7 at all times. In this way, detection of the status of deterioration of the lubricating agent 5 within the bearing assembly with the lubricant deterioration detecting device 1 can be accomplished stably and with a high precision.

Also, if the lubricant deterioration detecting device 1 is fitted with the arcuate covering 12 having been arranged in a coaxial relation with the seal casing 28, the lubricant deterioration detecting device 1 can easily be positioned within the bearing assembly 20 and assemblage can be facilitated. It is to be noted that the fitting of the lubricant deterioration detecting device 1 in this case may not be always limited to press fitting, but such fitting may be accomplished by employing a suitable connecting process such as, for example, one or more of screwing and bonding can be employed.

Wirings 35 for connecting the light emitting element 2 with the light emitting circuit 9 and the light receiving element 3 with the light receiving circuit 9, respectively in the lubricant deterioration detecting device 1, are connected with the light emitting circuit 8 and the light receiving circuit 9, both positioned outside the bearing assembly 20, after having extended from the inside of the lubricant deterioration detecting device 1 through a hole 36 defined in the seal casing 28. That hole 36 defined in the seal casing 28 is internally covered by the arcuate covering 12 of the lubricant deterioration detecting device 1 and is further sealed by the elastic element 37 so as to have a water resistant property.

The other bearing sealing element 31A is also fitted to the bearing outer ring 22 by means of a sealing unit 27A. This sealing unit 27A is rendered to be of a structure identical with the sealing unit 27, other than no lubricant deterioration detecting device 1 being fitted thereto.

It is to be noted that the light emitting circuit 8 and the light receiving circuit 9 may be disposed inside the bearing assembly 20. Where no space is available outside the bearing assembly 20 for accommodating the circuits, the arcuate covering 12 of the lubricant deterioration detecting device 1 has to be extended in the circumferential direction and the light emitting circuit 8 and the light receiving circuit 9 are then arranged on the covering 12, thereby facilitating disposition of those circuits within the bearing assembly 20.

According to the detector equipped bearing assembly 20 of the construction hereinabove described, the status of deterioration of the lubricating agent sealed within the bearing assembly can be accurately detected on a real time basis. Accordingly, prior to the occurrence of an abnormality in operation of the bearing assembly 20, the necessity of replacement of the lubricating agent can be determined and any undesirable damage to the bearing assembly, which would result from failure to lubricate the bearing assembly 20, can be avoided. Also, since the necessity of the replacement of the lubricating agent is determined in reference to the output of the lubricant deterioration detecting device 1, the amount of the lubricating agent to be disposed before the expiration date of use can be reduced.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

What is claimed is:

1. A detector equipped bearing assembly having a lubricant deterioration detecting device, the lubricant deterioration detecting device being fitted to a rolling bearing assembly, the lubricant deterioration detecting device comprising:
    an optical fiber of an arcuate shape having one end positioned in face-to-face relation with a light emitting element and also having the opposite end positioned in face-to-face relation with a light receiving element, the arcuate shape corresponding to the circumferential shape of inner and outer rings of the rolling bearing assembly;
    a measuring gap defined in a portion of the arcuate optical fiber for receiving a lubricating agent inserted therein; and
    a deformable resistance element provided in proximity to the measuring gap, of which amount of deformation changes with change of the state of lubrication with the lubricating agent, the resistance element being positioned within a bearing space delimited between the inner and outer rings of the rolling bearing assembly.

2. The detector equipped bearing assembly as claimed in claim 1, wherein the resistance element has a member comprising a deformable piece protruding at right angles to a base end thereof.

3. The detector equipped bearing assembly as claimed in claim 1, wherein the resistance element is a hinge structure having its angle variable at a hinge portion thereof.

4. The detector equipped bearing assembly as claimed in claim 1, wherein the resistance element has a planimetric shape, which is effective to move the lubricating agent in at least two of a direction along an arc center axis relative to the arcuate shape of the optical fiber, a radial direction thereof and a circumferential direction thereof.

* * * * *